(12) United States Patent
Hu et al.

(10) Patent No.: US 10,925,854 B2
(45) Date of Patent: Feb. 23, 2021

(54) METHODS AND COMPOSITIONS FOR PREVENTING OR TREATING FATTY LIVER, PROTECTING LIVER FUNCTION OR AMELIORATING LIVER DISEASES CAUSED BY FATTY LIVER OR OTHER ASSOCIATED DISORDERS

(71) Applicant: SINEW PHARMA INC., Taipei (TW)

(72) Inventors: Oliver Yoa-Pu Hu, Taipei (TW); Hsin-Tien Ho, Taipei (TW); Yung-En Wu, Taipei (TW); Hsi-Hui Tang, Taipei (TW)

(73) Assignee: SINEW PHARMA INC., Taipei (TW)

( * ) Notice: Subject to any disclaimer, the term of this patent is extended or adjusted under 35 U.S.C. 154(b) by 0 days.

(21) Appl. No.: 15/564,507

(22) PCT Filed: Mar. 31, 2016

(86) PCT No.: PCT/CN2016/078039
§ 371 (c)(1),
(2) Date: Oct. 5, 2017

(87) PCT Pub. No.: WO2017/084234
PCT Pub. Date: May 26, 2017

(65) Prior Publication Data
US 2018/0117003 A1 May 3, 2018

Related U.S. Application Data

(60) Provisional application No. 62/257,697, filed on Nov. 19, 2015.

(51) Int. Cl.
| | |
|---|---|
| *A61K 31/357* | (2006.01) |
| *A23L 33/10* | (2016.01) |
| *A61K 31/7004* | (2006.01) |
| *A23L 3/3472* | (2006.01) |
| *A61K 31/7048* | (2006.01) |
| *A61P 1/16* | (2006.01) |
| *A61K 31/045* | (2006.01) |
| *A61K 31/047* | (2006.01) |
| *A61K 31/352* | (2006.01) |
| *A61K 31/353* | (2006.01) |
| *A61K 31/428* | (2006.01) |
| *A61K 31/7016* | (2006.01) |
| *A61K 31/7034* | (2006.01) |

(52) U.S. Cl.
CPC .......... *A61K 31/357* (2013.01); *A23L 3/3472* (2013.01); *A23L 33/10* (2016.08); *A61K 31/045* (2013.01); *A61K 31/047* (2013.01); *A61K 31/352* (2013.01); *A61K 31/353* (2013.01); *A61K 31/428* (2013.01); *A61K 31/7004* (2013.01); *A61K 31/7016* (2013.01); *A61K 31/7034* (2013.01); *A61K 31/7048* (2013.01); *A61P 1/16* (2018.01)

(58) Field of Classification Search
None
See application file for complete search history.

(56) References Cited

U.S. PATENT DOCUMENTS

| 5,080,910 A * | 1/1992 | Cherukuri | ............ A23G 3/346 426/3 |
|---|---|---|---|
| 2008/0214499 A1* | 9/2008 | Oku | ............ A23D 9/007 514/61 |
| 2013/0190354 A1 | 7/2013 | Wen et al. | |
| 2015/0051143 A1* | 2/2015 | Harada | ............ A61K 31/232 514/6.5 |

FOREIGN PATENT DOCUMENTS

CN 103179957 A 6/2013

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
Miyake, Y., Minato, K. I., Fukumoto, S., Shimomura, Y., & Osawa, T. (2004). Radical-scavenging activity in vitro of lemon peel fermented with Aspergillus saitoi and its suppressive effect against exercise-induced oxidative damage in rat liver. Food science and technology research, 10(1), 70-74. (Year: 2004).*
Qiu, L. X., & Chen, T. (2015). Novel insights into the mechanisms whereby isoflavones protect against fatty liver disease. World Journal of Gastroenterology: WJG, 21(4), 1099. (Year: 2015).*
International Search Report, issued in PCT/CN2016/078039, dated Sep. 1, 2016.

* cited by examiner

*Primary Examiner* — Dale R Miller
(74) *Attorney, Agent, or Firm* — Birch, Stewart, Kolasch & Birch, LLP (57) ABSTRACT

The present invention relates to methods and compositions for preventing or treating fatty liver, protecting liver function or ameliorating liver diseases caused by fatty liver or other associated disorders.

15 Claims, 1 Drawing Sheet

METHODS AND COMPOSITIONS FOR PREVENTING OR TREATING FATTY LIVER, PROTECTING LIVER FUNCTION OR AMELIORATING LIVER DISEASES CAUSED BY FATTY LIVER OR OTHER ASSOCIATED DISORDERS

CROSS REFERENCE TO RELATED APPLICATIONS

This application is the National Phase of PCT International Application No. PCT/CN2016/078039, filed on Mar. 31, 2016, which claims priority under 35 U.S.C. 119(e) to U.S. Provisional Application No. 62/257,697, filed on Nov. 19, 2015, all of which are hereby expressly incorporated by reference into the present application.

TECHNOLOGY FIELD

The present invention relates to methods and compositions for preventing or treating fatty liver, protecting liver function or ameliorating liver diseases caused by fatty liver or other associated disorders.

BACKGROUND OF THE INVENTION

The liver is a part of the digestive system in the animal body, and also the major organ that produces and secretes a lot of digestive juices. The liver also has functions of absorption, metabolism, detoxification, and immune protection, etc. The liver is a vital organ in the metabolism of fat and plays a major role in the digestion, absorption, decomposition, synthesis and transport of fatty foods. The free fatty acid (FFA) ingested by the liver from the blood will eventually be synthesized into triglyceride (TG), which is then stored in the liver or transported out of the liver and into the blood circulation in the form of very low density lipoprotein (VLDL). Therefore, once the liver is damaged, lipids (especially TG) will be abnormally metabolized and accumulated in the liver cells.

Under normal circumstances, fat accounts for 3% by weight of the liver. Clinically, "fatty liver disease (FLD)" means that fat in the liver exceeds 5% by weight of the liver, or more than 10% of the liver cells show vesicular fatty changes in the liver tissue sections[2]. According to the causes of diseases, fatty liver can be divided into alcoholic fatty liver diseases (AFLD), non-alcoholic fatty liver diseases (NAFLD), or other fatty liver diseases derived from other factors, such as drugs. Fatty liver diseases are pathologically characterized by the appearance of fatty metamorphosis or steatosis, steatohepatitis, or the like. By the percentage of liver cells suffering from steatosis, fatty liver is categorized as mild (<33%), moderate (33-66%) and severe (>66%)[3,9,21]. Previously, fatty liver was considered a benign and reversible condition, and thus less taken seriously, but recent studies had found that it will lead to severe liver fibrosis and cirrhosis, and even liver cancer. As the population of obese people increases, the prevalence of FLD also increases.

The main cause of liver diseases in European and American countries is chronic excessive drinking, and therefore the vast majority of liver diseases are caused by alcohol lesions. But over the past 15-20 years, NAFLD has become the first cause of diseases to be considered for liver dysfunction in European and American countries[2]. Thaler described NAFLD in 1962. In 1980, Ludwig proposed "Non-alcoholic steatohepatitis (NASH)" from accompanying NAFLD found in a group of obese female patients with diabetes and hyperlipidemia. Thereafter, in 1986, Schaffner emphasized again that NASH played an important role in the mechanism of fibrosis derivation in the course of NAFLD[21]. Until 1998, Day found that 15-50% of patients with NASH were suffered from different degrees of fibrosis derivation[4], so clinicians started to pay attention to NAFLD. Nowadays, in addition to AFLD, NASH is not merely a stage in the natural progression of NAFLD in clinical practice; due to the presence of NASH, NAFLD is no longer considered a benign liver disease.

Currently, in the study of FLD in North America, South America, Japan, Northern Europe, Southern Europe, Australia and the Middle East, it is found that, the prevalence of NAFLD is at least 10-39%, and the postmortem autopsy histopathological examination showed that the prevalence of NAFLD is around 20%, in which the incidence of accompanying NASH is approximately 3-18%. The prevalence of NAFLD among obese people is up to 57-74% (4.6 times of that among normal people), of which 20-25% was found suffering from NASH lesions, and 2-3% suffering from cirrhosis. During the past three decades in Taiwan, the prevalence of NAFLD also increased year by year due to the improvement of economic environment and diet. In recent years, the prevalence of NAFLD in Taiwan has become 12-37%, which is close to that in Japan (9-13%), and the prevalence of NAFLD among non-obese people is about 10%, while that among morbid obese people (with BMI greater than 30) is as high as 80%[15,23].

Regarding the mechanism of NAFLD, in the United Kingdom, Day and James proposed the Two-hit hypothesis based on a large number of clinical researches and animal experiments. Fatty liver occurs upon the first hit, and steatohepatitis occurs upon the second hit. The first hit is prompted by excessive accumulation of fat in the liver, which is caused by obesity, hyperlipidemia, etc. The second hit is due to oxidative stress and the effect of reactive oxygen species (ROS) in mitochondria, resulting in lipid peroxidation on the liver cell membrane, release of original inflammatory cytokines and free radicals, and fibrosis due to activation of stellate cells, and leading to liver cell necrosis[4,5,19]. The mechanism of NASH involves the peroxidation of triglyceride, oxidative stress, ROS response, increased peroxidation of lipids in liver cells, or increase of cytokines and liver enzymes, leading to a series of autoimmune interactions[12].

The causes of fatty liver are mostly associated with long-term excessive intake of animal fat, protein, carbohydrates, excess calories transforming into fat accumulated in the body, leading to obesity and fatty liver. Patients with fatty liver may have normal blood GOT/GPT values. Therefore, a correct diagnosis of fatty liver must use the abdominal ultrasound, which currently provides more than 97% accuracy.

Currently, there is no ideal drug with specific therapeutic effect over FLD, the treatment guidelines of which aim at improving the potential risk factors or controlling the progress of chronic diseases by using drugs. It is recommended to apply symptomatic treatments according to the causes of fatty liver. For example, those who suffering from fatty liver caused by overweight should lose weight moderately. Anyone with alcoholic fatty liver needs to quit drinking and eats a balanced diet for improving the conditions. Chemicals or drugs that damage liver and lead to fatty liver diseases through long-term contact shall immediately be stopped using. Fatty liver caused by diseases, such as hepatitis C, high blood fat, etc., shall be treated by treating the original diseases, such as treating hepatitis C or controlling blood lipids. If excessive triglycerides are caused by physical factors, fatty liver diseases cannot be ameliorated by losing weight.

However, the drugs that are commonly used in clinical to lower serum triglycerides and cholesterol are often accompanied with side effects, for example, hepatotoxicity, myopathy such as myalgia, myositis, rhabdomyolysis, and the like. Regarding the lipid-lowering drugs, muscle toxicity is the most notable side effect. Especially, Statins shows the highest occurrence of muscle toxicity, and fibric acid follows. In addition, the lipid-lowering drugs have a "fat driving" effect, which "drives" blood lipids to the liver, where fat accumulation already exists and therefore the large influx of lipids would be difficult to be processed, leading to excessive accumulation of fat in the liver and making fatty liver worse. It can be seen that the lipid-lowering drugs are not suitable for the treatment of FLD.

Therefore, there is still a need to find an effective ingredient for preventing and treating fatty liver and liver diseases caused by fatty liver, protecting liver function, and ameliorating associated disorders.

SUMMARY OF THE INVENTION

The present invention provides one or more excipients (including flavonoid compounds) having the efficacies of preventing or treating fatty liver, protecting liver function or ameliorating liver diseases caused by fatty liver or other associated disorders, wherein the compound is selected from the group consisting of sodium lauryl sulfate, menthol, sucralose, mannitol, sorbitol, saccharin, glycerin, sodium benzoate, oxide red, pregelatinized starch, sodium cyclamate, sorbic acid, lemon oil, citric acid, butylated hydroxyanisole, poncirin, isovitexin, eriodictyol, ergosterol, β-myrcene, hyperoside, (+)-catechin, galangin, morin, sciadopitysin, didymin, gossypin, luteolin-7-glucoside, (+)-taxifolin, trans-cinnamic acid, diosmin, linarin, xylitol, luteolin, swertiamarin, and any combinations thereof.

Therefore, in one aspect, the present invention provides use of the compound as described herein for manufacturing a composition for preventing or treating fatty liver, protecting liver function or ameliorating liver diseases caused by fatty liver or other associated disorders. The present invention also provides a method of preventing or treating fatty liver, protecting liver function or ameliorating liver diseases caused by fatty liver or other associated disorders by administering the compound.

In some embodiments, the compound is selected from the group consisting of sodium lauryl sulfate, menthol, sucralose, mannitol, sorbitol, saccharin, glycerin, sodium benzoate, oxide red, pregelatinized starch, sodium cyclamate, sorbic acid, lemon oil, citric acid, butylated hydroxyanisole, and any combinations thereof.

In some embodiments, the compound is selected from the group consisting of poncirin, isovitexin, eriodictyol, ergosterol, β-myrcene, hyperoside, (+)-catechin, galangin, morin, sciadopitysin, didymin, gossypin, luteolin-7-glucoside, (+)-taxifolin, trans-cinnamic acid, diosmin, linarin, xylitol, luteolin, swertiamarin, and any combinations thereof.

In some embodiments, the compound is selected from the group consisting of eriodictyol, mannitol, menthol, sucralose, saccharin, and any combinations thereof.

In some embodiments, the compound is selected from the group consisting of (1) a combination of saccharin and mannitol, (2) a combination of menthol and mannitol, (3) a combination of sucralose and mannitol, (4) a combination of eriodictyol and mannitol, (5) a combination of eriodictyol and sucralose, (6) a combination of menthol, mannitol and eriodictyol, and (7) a combination of sucralose, mannitol and eriodictyol.

In some embodiments, one or more compounds described herein is administered with one or more compound selected from the group consisting of puerarin, phloridzin, sinensetin, (−)-epigallocatechin, kaempferol, ursolic acid, silymarin, (+)-limonene, hesperidin, (−)-epicatechin-3-gallate, silybin, formononetin, myristic acid ethyl ester, eicosapentaenoic acid (EPA), wongonin, povidone K-30, protocatechuic acid, umbelliferone, hesperitin, nordihydroguaiaretic acid, neohesperidin, naringin, (−)-epicatechin, glycyrrhizin, baicalin, quercitrin, and baicalein.

In some embodiments, the compound of the present invention can reduce a liver fat content of a subject.

In some embodiments, the compound of the present invention can reduce a fat content in the liver cells of a subject.

In some embodiments, the compound of the present invention can reduce liver damages of a subject, such as liver tissue damages or liver dysfunction.

In some embodiments, the compound of the present invention can enhance liver antioxidant activities of a subject.

In some embodiments, the compound of the present invention can be used to ameliorate associated disorders caused by various types of liver fat accumulation, including, but not limited to, fatty liver diseases, acute and chronic alcoholic fatty liver diseases, acute and chronic non-alcoholic fatty liver diseases, acute and chronic alcoholic hepatitis, acute and chronic non-alcoholic steatohepatitis, non-alcoholic cirrhosis and alcoholic cirrhosis (ICD-9-CM diagnosis Codes: 571.8, 571.0, 571.1, 571.2, 571.3, 571.4, 571.5, 571.9).

In some embodiments, the subjects who are suitable to take the compound of the present invention are patients with fatty liver diseases or obese people.

In some embodiments, the compound of the present invention can be formulated into a drug, a food additive, or health food.

In another aspect, the present invention provides a composition, which includes any two or more compounds selected from those described above.

In some embodiments, the composition of the present invention includes any two or more compounds selected from the group consisting of eriodictyol, mannitol, menthol, sucralose and saccharin.

In some embodiments, the composition of the present invention includes a combination selected from the group consisting of (1) a combination of saccharin and mannitol, (2) a combination of menthol and mannitol, (3) a combination of sucralose and mannitol, (4) a combination of eriodictyol and mannitol, (5) a combination of eriodictyol and sucralose, (6) a combination of menthol, mannitol and eriodictyol, and (7) a combination of sucralose, mannitol and eriodictyol.

It is believed that the present invention can be utilized to its widest extent by those skilled in art based on the foregoing description without further explanation. Therefore, it will be understood that the following description is illustrative only and not to limit the remainder of the disclosure in any way.

BRIEF DESCRIPTION OF THE DRAWINGS

The embodiment is shown below to illustrate the present invention. It should be understood, however, that the present invention is not limited to the preferred embodiment shown. In the drawing.

DETAILED DESCRIPTION OF THE INVENTION

All technical and scientific terms used herein have the meanings as generally understood by those skilled in the art, unless otherwise indicated.

As used herein, the term "a" or "an" refers to at least one (one or more than one) with respect to the number, unless otherwise indicated.

The present invention discloses that one or more of the compounds described above have the effects in reducing a liver fat content and ameliorating associated disorders. Thus, the present invention provides use of a compound described herein for manufacturing a composition for preventing or treating fatty liver, protecting liver function, or ameliorating liver diseases caused by fatty liver or other associated disorders. The present invention also provides a method of preventing or treating fatty liver, protecting liver function, or ameliorating liver diseases caused by fatty liver or other associated disorders. The method includes administering to a subject in need an effective amount of the compound as described herein. The present invention also provides a composition for preventing or treating fatty liver, protecting liver function, or ameliorating liver diseases caused by fatty liver or other associated disorders.

As used herein, the term "liver fat content" refers to the content of fat that is accumulated in the liver of a subject wherein the fat includes generally defined lipids, such as triglyceride (TG) and cholesterol. As used herein, the term "reducing liver fat content" generally refers to reduction of the content of abnormal liver fat in a subject, i.e. to decrease the content of abnormal liver fat and, more particularly, to lower the content of abnormal liver fat to a normal level. For example, under normal circumstance, fat accounts for 3% by weight of the liver. If fat in the liver exceeds 5% by weight of the liver, it is determined as abnormal fat accumulation (The liver fat content described above is a relative percentage for exemplification, and may vary due to ethnicity and other factors). In a specific embodiment, the term "reducing liver fat content" used herein can mean that the content of abnormal liver fat in a subject is reduced, for example, from 5% by weight of the liver or more to 3% by weight of the liver. A liver fat content can be assessed by standard analytical methods, including but not limited to ultrasound analysis, magnetic resonance imaging (MRI), magnetic resonance spectroscopy (MRS), computed tomography (CT), and liver biopsy.

As used herein, the term "liver function" refers to one or more physiological functions performed by the liver. Liver function can be analyzed by many routine assays, such as alanine aminotransferase (ALT) analysis or aspartate transaminase (AST) analysis. According to the present invention, the compound described herein can be used to protect liver functions, including improving liver functions and preventing the liver from damage.

As used herein, the term "liver disease" refers to liver cell injuries or damages caused by certain factors, which then potentially lead to liver dysfunction. According to the present invention, the compound described herein can be used to ameliorate liver diseases caused by fatty liver. More particularly, the term "liver damage(s)" used herein refers to liver with histological or biochemical dysfunction, as compared with normal liver. In a specific embodiment, as used herein, the term "liver damages" refers to liver lesions caused by alcoholic or non-alcoholic factors, such as high fat diet or obesity. In a specific embodiment, the term "liver damages" could be liver tissue damages with one or more characteristics selected from steatosis, lobular inflammation, hepatocyte ballooning, and vesicular fat droplets produced by liver cells. In a specific embodiment, the term "liver damages" can be biochemical dysfunction of liver, which can be determined from the activity of alanine aminotransferase (ALT) or aspartate transaminase (AST). Higher activity levels of ALT or AST indicate severer dysfunction of liver's biochemical functions.

As used herein, the term "liver antioxidant activity" refers to the activity or ability against oxidative stress. Enhancement of liver antioxidant activities of a subject by the compound according to the present invention includes, but is not limited to, reducing oxidative stress or enhancing enzyme activities or contents of the members of antioxidant systems. The members of antioxidant systems may be glutathione peroxidase (GPx), glutathione (GSH), glutathione reductase (GRd), and/or superoxide dismutase (SOD).

According to the present invention, the compound described herein includes common excipients and bioflavonoids, which may be used to reduce liver fat contents and ameliorate associated disorders. The term "associated disorders" described herein includes the disorders caused by abnormal accumulation of liver fat, which include but is not limited to fatty liver diseases, acute and chronic alcoholic fatty liver diseases, acute and chronic non-alcoholic fatty liver diseases, acute and chronic alcoholic hepatitis, acute and chronic non-alcoholic steatohepatitis, non-alcoholic cirrhosis and alcoholic cirrhosis (ICD-9-CM Diagnosis Codes: 571.8, 571.0, 571.1, 571.2, 571.3, 571.4, 571.5, 571.9).

As used herein, the term "preventing" refers to preventive or avoidance measures for a disease or symptoms or conditions of a disease, which include but are not limited to applying or administering one or more active agents to a subject who has not yet been diagnosed as a patient suffering from the disease or the symptoms or conditions of the disease but may be susceptible or prone to the disease. The purpose of the preventive measures is to avoid, prevent, or postpone the occurrence of the disease or the symptoms or conditions of the disease.

As used herein, the term "treating" refers to the therapeutic measures to a disease or the symptoms or conditions of a disease, which include but are not limited to applying or administering one or more active agents to a subject suffering from the disease or the symptoms or conditions of the disease or exacerbation of the disease. The purpose of the therapeutic measures is to treat, cure, mitigate, relieve, alter, remedy, ameliorate, improve, or affect the disease, the symptoms or conditions of the disease, disability caused by the disease, or exacerbation of the disease.

As used herein, the term "individual" or "subject" includes human or non-human animals, in particular mammal, for example, companion animals (such as dogs, cats and the like), farm animals (such as cattle, sheep, pigs, horses, etc.), or laboratory animals (such as rats, mice, guinea pigs, etc.).

As used herein, the term "effective amount" refers to the amount of an active ingredient achieving desired biological efficacy or therapeutic effects in a subject being treated, for example, reducing a liver fat content in the subject or ameliorating associated disorders.

For the purpose of transport and uptake, an effective amount of an active ingredient according to the present invention may be formulated with a pharmaceutically acceptable carrier to form a suitable form of a pharmaceutical composition. According to the routes of administration, the pharmaceutical composition of the present invention preferably comprise from about 0.1% to about 100% by weight of the active ingredient, based on the total weight of the composition.

As used herein, the term "pharmaceutically acceptable" means that the carrier is compatible with the active ingredient of the composition (and does not affect the effect of the active ingredient), and, preferably, the carrier may stabilize the active ingredient and is safe for the subjects being treated. The carrier may be a diluent, a vehicle, an excipient, or a medium for the active ingredient. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The composition may additionally comprise lubricants such as talc, magnesium stearate, and mineral oil; wetting agents; emulsifying and suspending agents; preservatives such as methyl and propyl paraben; sweetening agents; and flavoring agent. After being administered to the patient, the composition of the present invention may provide effects of rapid, sustained or delayed release of the active ingredient.

According to the present invention, the composition may be in any form, for example, tablets, pills, powders, lozenges, capsules, flat capsules, elixirs, suspensions, emulsions, solutions, syrups, soft and hard gelatin capsules, suppositories, sterile injectable solutions, and packaging powders.

The composition of the present invention may be administered via any physiologically acceptable routes, e.g., oral, parenteral (such as intramuscular, intravenous, subcutaneous, and intraperitoneal), transdermal, suppository, and nasal methods. Parenteral administration preferably uses a sterile aqueous solution, which may contain other substances, such as salts or glucose that is sufficient to make the solution have the same tension as blood. The aqueous solution may be suitably buffered (preferably having a pH of 3-9) as required. Those skilled in the art may prepare suitable parenteral compositions by known standard pharmacological techniques under sterile conditions.

The present invention will be further illustrated by the following embodiments, which are provided for demonstration purposes only, and not limitation of the present invention. It will be apparent to those skilled in the art that various modifications can be made to the particular embodiments disclosed by the present invention without departing from the spirit and scope of the present invention and still get the same or similar results.

EXAMPLES

1. Materials and Methods
1.1 Cell Lines and Cell Culture Media

The activity of the various compounds of the present invention in reduction of fat content was analyzed by using human hepatoma cell line Hep G2.

Dulbecco's Modified Eagle's Medium (DMEM) was used to prepare DMEM culture Nos. A-F listed in Table 1 for carrying out subsequent experiments.

TABLE 1

Preparations of DMEM culture Nos. A-F.

| DMEM cultures | Preparation methods |
| --- | --- |
| No. A | DMEM was dissolved in 1,400 mL of water with stirring, and then 2 g of 4-(2-hydroxyethyl)-1-piperazine-ethanesulfonic acid (HEPES) was added, to which a sodium bicarbonate solution (4 g of sodium bicarbonate powder dissolved in 400 mL of water by stirring) was added, and the volume was made up to 2,000 mL with water. The pH of the resulting solution was adjusted to 7.3 ± 0.05 by adding 5N HCl. After being filtered through a 0.2 μm sterile membrane, the final solution was dispensed into sterile serum vials and stored at 4° C. |
| No. B | 50 mL of deactivated fetal bovine serum (FBS), 5 mL of sodium pyruvate (100 mM), 5 mL of penicillin (100 U/mL) and streptomycin (100 U/mL), and 5 mL of MEM non-essential amino acid solution(100X) were added into 450 mL of DMEM culture No. A. |
| No. C | 5 mL of sodium pyruvate (100 mM), 5 mL of penicillin (100 U/mL) and streptomycin (100 U/mL), and 5 mL of MEM non-essential amino acid solution(100X) were added into 450 mL of DMEM culture No. A. |
| No. D | DMEM culture No. B was added into the oleate/albumin complex. The oleate/albumin complex was prepared according to the method published by Van Harken et al. in 1969 (J Biol Chem. 1969 May 10; 244(9): 2278-85). The method includes taking 25 mL of DMEM culture No. A, into which 5 g of bovine serum albumin (BSA) was added, and then 5N sodium hydroxide solution was added to adjust the pH to 7.4 to form a mixture. The mixture was then placed in an ice bath at 0° C. to form the BSA solution. Oleic acid was dissolved in 50 ml of alcohol (95%) and then titrated to the phenolphthalein titration endpoint with 1N sodium hydroxide solution. The alcohol was blown away by flowing helium. The resulting sodium oleate was dissolved in DMEM culture No. A at 37° C. to form a sodium oleate solution. At last, the BSA solution was added dropwise into the sodium oleate solution with stirring to form the oleate/albumin complex solution. |

TABLE 1-continued

Preparations of DMEM culture Nos. A-F.

| DMEM cultures | Preparation methods |
|---|---|
| No. E | Various amounts of silymarin were dissolved in DMEM culture No. C. |
| No. F | Various amounts of the test compounds of the present invention were dissolved in DMEM culture No. C. |

The DMEM cultures Nos. A-F were preserved at 2-8° C., and warmed up in a water bath at 37° C. before experiments.

1.2 Cell Counts and Survivability Test

Dead cells would take up 0.4% trypan blue and then show a color; whereas live cells would exclude the dyes due to the intact cell membranes and show a clear color. 100 μl of cell suspension and equal volume of 0.4% trypan blue were mixed uniformly to form a mixture. Some of the mixture (about 20 μl) was added into the groove above the chamber of the hemocytometer, which was then covered with a cover slip for observing under the optical microscope. Live cells were not stained, and dead cells were blue.

1.3 Formation of Fatty Liver Cells from HepG2 Cell Lines by Induction with Oleic Acid HepG2 cell lines ($15 \times 10^6$ cells) were cultured in DMEM culture No. B, incubated in an incubator with 5% $CO_2$ at 37° C. for 24 hours, cultured in DMEM culture No. C (serum-free medium) for 24 hours, and finally cultured in DMEM culture No. D (containing oleate/albumin complex) for another 48 hours to induce HepG2 cell lines to form fatty liver cells.

1.4 Treatments for Each Group of Fatty Liver Cells

HepG2 cell lines were divided into six groups, including: (1) Blank: no treatment; (2) DMSO group: cells from Blank were treated with dimethyl sulfoxide (DMSO); (3) Control: induction with oleic acid to form fatty liver cells; (4) Vehicle group: fatty liver cells formed by induction with oleic acid were treated with DMSO; (5) Positive control: fatty liver cells were treated with silymarin; and (6) Test Group: fatty liver cells were treated with various compounds of the present invention.

1.5 Determination of TG in Cells

After incubation for 72 hours, the treated cells from each group were successively washed twice with PBS, and then incubated with 0.5 ml of trypsin/EDTA for 3 minutes. Afterwards, the cells were scraped with 2 ml of PBS and then transferred to the centrifuge tube to be shattered by ultrasonic. 20 μl of the cell extracts was taken to determine the content of protein. TG determination was performed using commercially available combination of agents (Randox). The TG content obtained above was divided by the protein content to obtain a ratio, representing a relative TG content in the cells.

1.6 Animals for Experiments

B6 mice recommended in the specification "Method for evaluating the liver protection and health care efficacies of health food" announced by the Department of Health were chosen for animal testing. More than four (4) mice were used in each group of the pre-test, while more than twelve (12) mice were used in each group of the confirmatory test. Male mice bred at 23±2° C. in an animal room with 55±15% relative humidity under normal light/dark cycle (7:00 AM-7:00 PM lights on/7:00 PM-7:00 AM lights off) and weighing 18-23 g were purchased from BioLASCO (Taipei) and housed at Laboratory Animal Center in National Defense Medical Center. The animal test was carried out according to the guideline for animal experiment of National Health Research Institutes. Mice were fed with normal feed at 3-5 g/day and unlimited supply of water for 1-2 weeks and investigated for health condition. The weight of mice was recorded once a week.

1.7 Animal Grouping

The tested animals were grouped randomly into Blank, High Fat Diet control (HFD), Positive Control (PS), and Test group. The animals of Blank were fed with normal feed. The animals of HFD were fed with high fat feed. The animals of PS were fed with high fat feed, and additionally fed with silymarin (5 mg/kg/day) by a tube. The animals of Test group were fed with high fat feed, and additionally force-fed with test compounds by a tube.

1.8 Test Methods

The animals of Blank were fed casually with normal feed for 12 weeks, while the animals of HFD, PS, and Test group were fed casually with high fat feed for 12 weeks. After 8 weeks of feeding, the animals of Blank and HFD were fed with deionized water by a tube once a day; the animals of PS were fed with silymarin by a tube once a day; and the animals of Test Group were fed with test compounds by a tube once a day for a duration of 4 or 8 weeks.

Before testing and in the eighth ($8^{th}$), twelfth ($12^{th}$), and sixteenth ($16^{th}$) week after testing, blood was collected from the cheek or the heart. At the end of testing, all mice were weighted and then sacrificed, and blood was collected from the cheek or the heart simultaneously. The blood specimens of mice was placed at room temperature for one hour to clot, and then the serum was separated by centrifugation in a refrigeration centrifuge at 15,700×g at 4° C. for 5 minutes. Afterwards, biochemical indices of liver function, including aspartate transaminase (AST), alanine aminotransferase (ALT), triglyceride (TG), total cholesterol (TCHO/TC), low-density lipoprotein cholesterol (LDL-C), and high-density lipoprotein cholesterol (HDL-C), were detected by the automatic blood biochemistry analyzer.

In addition, abdominal fat and liver specimens were taken from the abdomens of sacrificed mice and weighted to compare the weight of fat and liver and obtain a ratio of liver weight to body weight. Two tissue blocks with a volume of approximately 1 $cm^3$ were cut from the largest right lobe of liver, fixed in 10% neutral formalin solution, and then embedded with paraffin for sectioning and H&E staining for histopathological observation. Moreover, the rest of the liver was frozen for preservation and detection of the contents of triglyceride and total cholesterol in the liver. Furthermore, the liver function of animals of each group were analyzed by Galactose Single Point Method, which was recognized and recommended for quantification of remaining liver function in clinical use by U.S. FDA and Ministry of Health and Welfare, Taiwan. At the end of the tests, 0.5 g of galactose (G.S.P.® 0.4 g/mL) per kg of animal was administered via intravenous. One hour after the administration, about 0.5 ml of whole blood was taken by using a filter paper to evaluate liver function of mice. The higher the value of GSP was, the worse the remaining liver function would be (FDA: "Guidance for Industry: Pharmacokinetics in Patients with Impaired. Hepatic Function—Study Design, Data Analysis and Impact on Dosing and. Labeling. 2003).

1.9 Histopathological Tissue Sectioning:

At the end of the test, all mice were sacrificed. One tissue block with a volume of approximately 1 cm³ was cut from the largest right lobe of liver, fixed in 10% neutral formalin, and then dehydrated and hyalinized in various concentrations of ethanol (30, 50, 70, 95, 99.5%) and xylene. Afterwards, xylene was replaced with hot paraffin solution. At last, the tissue was embedded with paraffin solution. The finished paraffin specimen was cut into 5 pun-thickness paraffin sections by the microtome. The sections were pasted on clean slides, dried at 37° C., and then stained by H&E staining.

1.10 Hematoxylin and Eosin Staining (H&E)

Liver tissue sections were deparaffinized in xylene for 30 minutes, and then successively rehydrated in 99.5%, 95%, 70%, 50%, and 30% ethanol for 30 minutes, respectively. After being soaked in distilled water for 10 minutes, the sections could be stained. The sections were first immersed in hematoxylin for 30 seconds to stain cell nuclei, then washed with distilled water for a few minutes, stained with eosin for 2-5 minutes, and washed with distilled water for a few minutes again. After staining process was finished, the sections were dehydrated successively in 50%, 70%, 95%, and 100% ethanol twice for 30 seconds, respectively, hyalinized twice in xylene, and finally sealed and stored with mounting media.

1.11 Histopathological Observation

In order to observe the changes of lesion, fat accumulation, necrosis, or fibrosis in liver cells when there was an ongoing liver damage, liver tissues were H&E stained to evaluate the degree of liver fat accumulation. All the histopathological sections were cut from the same position on the largest right lobe of liver for eliminating bias in subjective observation, and then subject to pathological staining. As for the assessment of semi-quantitative analysis in pathology, it had to be confirmed by a physician or a veterinary pathologist who conducted a double-blind analysis to score (NAS score)[16] and compare all the sections without knowing the test design. At last, the differential analysis of each group was performed by statistical methods.

1.12 Analysis of Liver Antioxidant Capacity

About 0.1 g of liver tissue was taken from the sacrificed animal and homogenized by centrifuge with a biomasher for 10 minutes. A 9-fold weight (w/w) of buffer (pH 7.4, 50 mmol/L Tris-HCl, 180 mmol/L KCl) was added to the homogenized tissue, which was then mixed well by a Vortex mixer for subsequent use. The resulting homogenization solution samples of liver tissue was used for the analysis of various members of liver antioxidant systems, including glutathione peroxidase (GPx), glutathione (GSH), glutathione reductase (Grd), and superoxide dismutase (SOD). Methods of related analysis can be found in the known literatures, for example, the draft of "Method for evaluating the liver protection and health care efficacies of health food" announced by the Ministry of Health and Welfare, Taiwan.

1.13 Statistical Analysis

All data were expressed as means 4 standard deviation (SD). Statistically significant difference of the test results was determined by calculation of one-way ANOVA using Statistical Package of the Social Science program, Version 13, SPSS Inc. Thereafter, multiple comparisons were carried out by using least significant difference method in post hoc test to confirm the significant difference between groups. The average difference between groups is judged to be significant when $p<0.05$.

2. Results 2.1 Cell Experiments

In cell experiments, the results of TG content reduction in HepG2 cells determined in Positive Control (silymarin) were shown in Table 2.

TABLE 2

Effects of silymarin in reduction of TG content in HepG2 fat cells of Positive Control

| Silymarin concentration (μM) | TG content in cells (μg/mg protein) | Reduction rate of TG (%) |
|---|---|---|
| 0 (Control) | 59.43 ± 4.60 | — |
| 1.0 | 44.17 ± 2.41 | 29 ± 8 |
| 5.0 | 44.59 ± 11.53 | 28 ± 10 |
| 10 | 26.38 ± 9.12 | 63 ± 11 |
| 100 | 20.48 ± 4.76 | 78 ± 5 |

The results of TG content reduction in HepG2 fat cells determined using constant concentrations of test compounds are shown in Table 3. The results show that the test compounds exhibited different degrees of effects in reduction of TG content in fatty liver cells formed from induced HepG2 cells under the condition of constant test concentrations, as compared with Control. The equation for calculating reduction rate (%) of TG was as follows: [1−(TG content of Test Group−TG content of Blank)/(TG content of Oleic acid induction Group−TG content of Blank)]×100%.

TABLE 3 the test compounds can reduce TG content in fatty liver cells.

| Tested substances (1.0 uM) | TG reduction rate (%) |
|---|---|
| silymarin Control | 35.33 ± 1.96 |
| puerarin | 49.91 ± 7.73 |
| phloridzin | 42.35 ± 6.05 |
| saidzein | 42.3 ± 5.34 |
| sodium lauryl sulfate | 38.73 ± 4.65 |
| poncirin | 38.12 ± 7.22 |
| sinensetin | 36.97 ± 4.84 |
| (−)-epigallocatechin | 36.78 ± 6.67 |
| kaempferol | 36.51 ± 4.78 |
| isovitexin | 35.93 ± 3.35 |
| ursolic Acid | 35.86 ± 8.92 |
| eriodictyol | 35.11 ± 0.87 |
| (+)-limonene | 35.02 ± 10.04 |
| hesperidin | 34.81 ± 5.25 |
| ergosterol | 34.19 ± 3.69 |
| β-myrcene | 33.97 ± 11.22 |
| (−)-epicatechin-3-gallate | 32.7 ± 4.33 |
| hyperoside | 30.51 ± 2.8 |
| silybin | 30.26 ± 3.24 |
| (+)-catechin | 29.57 ± 4.02 |
| formononetin | 29.55 ± 1.44 |
| myristic acid ethyl ester | 28.88 ± 3.91 |
| galangin | 28.11 ± 8.62 |
| sucralose | 26.68 ± 2.93 |
| eicosapentaenoic acid (EPA) | 26.15 ± 6.14 |
| morin | 25.84 ± 10.65 |
| mannitol | 22.35 ± 5.74 |
| sciadopitysin | 21.83 ± 5.04 |
| wongonin | 20.78 ± 1.12 |
| didymin | 20.37 ± 12.69 |
| gossypin | 20.25 ± 4.63 |
| sorbitol | 20.06 ± 2.57 |
| luteolin-7-glucoside | 19.33 ± 4.59 |
| povidone K-30 | 18.93 ± 5.13 |
| protocatechuic acid | 18.57 ± 7.6 |
| (+)-taxifolin | 17.91 ± 8.35 |

TABLE 3-continued the test compounds can reduce TG content in fatty liver cells.

| Tested substances (1.0 uM) | TG reduction rate (%) |
|---|---|
| saccharin | 17.53 ± 6.96 |
| umbelliferone | 17.4 ± 2.57 |
| glycerrin | 16.23 ± 4.25 |
| hesperitin | 16.08 ± 5.55 |
| nordihydroguaiaretic acid | 15.92 ± 2.3 |
| trans-Cinnamic Acid | 15.85 ± 0.82 |
| sodium benzoate | 14.35 ± 4.86 |
| oxide red | 13.59 ± 2.08 |
| neohesperidin | 13.29 ± 7.21 |
| naringin | 12.69 ± 3.72 |
| diosmin | 11.86 ± 3.73 |
| (−)-epicatechin | 10.76 ± 8.92 |
| glycyrrhizin | 10.55 ± 7.4 |
| linarin | 9.24 ± 12.34 |
| baicalin | 9.21 ± 6.21 |
| quercitrin | 9.15 ± 9.24 |
| xylitol | 7.36 ± 6.34 |
| baicalein | 7.09 ± 10.88 |
| luteolin | 6.95 ± 15.23 |
| swrtiamarin | 6.72 ± 11.04 |
| butylated hydroxyanisole | 6.21 ± 3.8 |
| sodium cyclamate | 4.77 ± 4.49 |
| menthol | 66.24 ± 1.87 |
| citric acid | 2.55 ± 4.43 |
| lemon oil | 0.56 ± 1.07 |
| pregelatinized starch | 7.18 ± 13.41 |
| sorbic acid | 2.03 ± 1.96 |

TABLE 3-1

Some of the test compounds from Table 3, showing reduction of TG content in fatty liver cells

| Tested substances (1.0 μM) | TG reduction rate (%) |
|---|---|
| puerarin | 49.91 ± 7.73 |
| phloridzin | 42.35 ± 6.05 |
| daidzein | 42.3 ± 5.34 |
| sinensetin | 36.97 ± 4.84 |
| (−)-epigallocatechin | 36.78 ± 6.67 |
| kaempferol | 36.51 ± 4.78 |
| ursolic Acid | 35.86 ± 8.92 |
| silymarin of Control | 35.33 ± 1.96 |
| (+)-limonene | 35.02 ± 10.04 |
| hesperidin | 34.81 ± 5.25 |
| (−)-epicatechin-3-gallate | 32.7 ± 4.33 |
| silybin | 30.26 ± 3.24 |
| formononetin | 29.55 ± 1.44 |
| myristic acid ethyl ester | 28.88 ± 3.91 |
| eicosapentaenoic acid (EPA) | 26.15 ± 6.14 |
| wongonin | 20.78 ± 1.12 |
| povidone K-30 | 18.93 ± 5.13 |
| protocatechuic acid | 18.57 ± 7.6 |
| umbelliferone | 17.4 ± 2.57 |
| hesperitin | 16.08 ± 5.55 |
| nordihydroguaiaretic acid | 15.92 ± 2.3 |
| neohesperidin | 13.29 ± 7.21 |
| naringin | 12.69 ± 3.72 |
| (−)-epicatechin | 10.76 ± 8.92 |
| glycyrrhizin | 10.55 ± 7.4 |
| baicalin | 9.21 ± 6.21 |
| quercitrin | 9.15 ± 9.24 |
| baicalein | 7.09 ± 10.88 |

TABLE 3-2

Some of the test compounds (bioflavonoids) from Table 3, showing reduction of TG content in fatty liver cells

| Tested substances (1.0 uM) | TG reduction rate (%) |
|---|---|
| poncirin | 38.12 ± 7.22 |
| isovitexin | 35.93 ± 3.35 |
| eriodictyol | 35.11 ± 0.87 |
| ergosterol | 34.19 ± 3.69 |
| β-myrcene | 33.97 ± 11.22 |
| hyperoside | 30.51 ± 2.8 |
| (+)-catechin | 29.57 ± 4.02 |
| galangin | 28.11 ± 8.62 |
| morin | 25.84 ± 10.65 |
| sciadopitysin | 21.83 ± 5.04 |
| didymin | 20.37 ± 12.69 |
| gossypin | 20.25 ± 4.63 |
| luteolin-7-glucoside | 19.33 ± 4.59 |
| (+)-taxifolin | 17.91 ± 8.35 |
| trans-Cinnamic Acid | 15.85 ± 0.82 |
| diosmin | 11.86 ± 3.73 |
| linarin | 9.24 ± 12.34 |
| xylitol | 7.36 ± 6.34 |
| luteolin | 6.95 ± 15.23 |
| swrtiamarin | 6.72 ± 11.04 |

TABLE 3-3

Some of the test compounds (excipients) from Table 3, showing reduction of TG content in fatty liver cells

| Tested substances (1.0 uM) | TG reduction rate (%) |
|---|---|
| sodium lauryl sulfate | 38.73 ± 4.65 |
| sucralose | 26.68 ± 2.93 |
| mannitol | 22.35 ± 5.74 |
| sorbitol | 20.06 ± 2.57 |
| saccharin | 17.53 ± 6.96 |
| glycerrin | 16.23 ± 4.25 |
| sodium benzoate | 14.35 ± 4.86 |
| oxide red | 13.59 ± 2.08 |
| butylated hydroxyanisole | 6.21 ± 3.8 |
| sodium cyclamate | 4.77 ± 4.49 |
| menthol | 66.24 ± 1.87 |
| citric acid | 2.55 ± 4.43 |
| lemon oil | 0.56 ± 1.07 |
| pregelatinized starch | 7.18 ± 13.41 |
| sorbic acid | 2.03 ± 1.96 |

2.2 Animal Experiments

In the animal experiments, all the animals were treated to induce fatty liver, except the animals of Blank that were fed with normal feed. After eight (8) weeks, the animals of each group were given different treatment for four (4) or eight (8) weeks in addition to the original feed. The animals of Blank and HFD were fed with deionized water; the animals of PS were fed with silymarin; and the animals of Test Group were fed with different test compounds, including puerarin, phloridzin, eriodictyol, sucralose, mannitol, saccharin, hesperitin, menthol, or combinations of some of them.

2.2.1 the Effects on Body Weight, Liver Weight, and Weight of Body Fat of Animals and Safety Evaluation of Test Compounds From the results of animal experiments, the liver weight, weight of body fat, and increase of body weight of animals of each group were shown in Table 4-1 and 4-2.

TABLE 4-1

The analysis results of liver weight and weight of body fat by test compounds.

| Items<br>Unit | Abdominal fat weight<br>g | Liver weight<br>g |
|---|---|---|
| Blank (n = 13) | 0.6 ± 0.2 *** | 1.6 ± 0.2 |
| HFD (n = 12) | 2.8 ± 0.4 | 1.6 ± 0.4 |
| Positive Control | | |
| silymarin 5.0 mg/kg (n = 6) | 2.0 ± 0.4 *** | 1.2 ± 0.3 *** |
| silymarin 1.5 mg/kg (n = 6) | 2.3 ± 0.5 * | 1.5 ± 0.1 |
| Single test compound | | |
| phloridzin 2.5 mg/kg (n = 6) | 2.3 ± 0.6 * | 1.3 ± 0.1 * |
| eriodictyol 2.5 mg/kg (n = 6) | 2.7 ± 0.6 | 1.3 ± 0.1 ** |
| sucralose 7.5 mg/kg (n = 6) | 2.4 ± 0.3 | 1.4 ± 0.1 |
| sucralose 1.5 mg/kg (n = 6) | 2.1 ± 0.6 ** | 1.5 ± 0.2 |
| menthol 1.5 mg/kg (n = 6) | 2.3 ± 0.6 * | 1.6 ± 0.2 |
| mannitol 7.5 mg/kg (n = 6) | 2.4 ± 0.3 | 1.4 ± 0.1 |
| mannitol 4.5 mg/kg (n = 6) | 2.7 ± 0.3 | 1.4 ± 0.2 |
| mannitol 1.5 mg/kg (n = 6) | 2.0 ± 0.3 *** | 1.4 ± 0.2 |
| saccharin 1.5 mg/kg (n = 3) | 2.3 ± 0.5 | 1.5 ± 0.1 |
| puerarin 2.5 mg/kg (n = 6) | 2.8 ± 0.3 | 1.4 ± 0.2 |
| hesperitin 2.5 mg/kg (n = 6) | 3.0 ± 0.5 | 1.5 ± 0.1 |
| combinations of two test compounds | | |
| saccharin + mannitol<br>1.5 mg/kg + 1.5 mg/kg (n = 6) | 2.7 ± 0.4 | 1.4 ± 0.2 |
| menthol + mannitol<br>4.5 mg/kg + 4.5 mg/kg (n = 6) | 3.0 ± 0.5 | 1.6 ± 0.3 |
| menthol + mannitol<br>1.5 mg/kg + 1.5 mg/kg (n = 6) | 2.3 ± 0.6 | 1.5 ± 0.3 |
| combinations of three test compounds | | |
| menthol + mannitol + eriodictyol<br>.5 mg/kg + .5 mg/kg + .8 mg/kg (n = 6) | 2.6 ± 0.6 | 1.4 ± 0.2 |

Data were expressed as means ± SD.
Statistical difference resulted from ANOVA and LSD was denoted by words.
* $p < 0.05$,  $p < 0.01$, * $p < 0.005$, as compared with HFD.
TG: triglyceride
TC: total cholesterol
hesperitin
puerarin
eriodictyol
phloridzin
mannitol
menthol
sucralose
saccharin

TABLE 4-2

The analysis results of increase of body weight by test compounds.

| Items | Increase of<br>body weight<br>Unit<br>g |
|---|---|
| Blank (n = 13) | 15.6 ± 7.9 |
| HFD (n = 12) | 14.0 ± 8.4 |
| Positive Control | |
| silymarin 5.0 mg/kg (n = 6) | 10.2 ± 12.7 |
| silymarin 1.5 mg/kg (n = 6) | 10.9 ± 4.3 |
| Single test compound | |
| phloridzin 2.5 mg/kg (n = 6) | 13.7 ± 10.7 |
| eriodictyol 2.5 mg/kg (n = 6) | 8.3 ± 6.7 |
| sucralose 7.5 mg/kg (n = 6) | 8.3 ± 5.4 |
| sucralose 1.5 mg/kg (n = 6) | 17.0 ± 5.6 |
| menthol 1.5 mg/kg (n = 6) | 19.6 ± 5.0 |
| mannitol 7.5 mg/kg (n = 6) | 10.3 ± 8.5 |
| mannitol 4.5 mg/kg (n = 6) | 11.1 ± 7.7 |
| mannitol 1.5 mg/kg (n = 6) | 10.9 ± 7.4 |
| saccharin 1.5 mg/kg (n = 3) | 27.7 ± 12.7** |
| puerarin 2.5 mg/kg (n = 6) | 21.7 ± 3.1* |
| hesperitin 2.5 mg/kg (n = 6) | 14.5 ± 8.3 |
| Combinations of two test compounds | |
| saccharin + mannitol<br>1.5 mg/kg + 1.5 mg/kg (n = 6) | 16.6 ± 6.4 |
| menthol + mannitol<br>4.5 mg/kg + 4.5 mg/kg (n = 6) | 15.6 ± 5.0 |
| menthol + mannitol<br>1.5 mg/kg + 1.5 mg/kg (n = 6) | 14.9 ± 6.3 |
| Combinations of three test compounds | |
| menthol + mannitol + eriodictyol<br>.5 mg/kg + .5 mg/kg + .8 mg/kg (n = 6) | 21.7 ± 3.9* |

Data were expressed as means ± SD.
Statistical difference resulted from ANOVA and LSD was denoted by words.

TABLE 4-2-continued

The analysis results of increase of body weight by test compounds.

| Items | Increase of body weight Unit g |
|---|---|

*p < 0.05,
**p < 0.01,
***p < 0.005, as compared with HFD.
TG: triglyceride
TC: total cholesterol
hesperitin
puerarin
eriodictyol
phloridzin
mannitol
menthol
sucralose
saccharin The results show that the weight of abdominal fat increases in animals when induced with fatty liver. Administration of test compounds, mannitol, menthol and sucralose, respectively, reduces the weight of abdominal fat in animals significantly.

In addition, no abnormal condition was observed in animals of Test Group after the test compounds were administered. No animal died during the test. Occurrence of diseases or clinical symptoms caused by the test compounds was not observed from necropsy studies of sacrificial animals after the tests. Therefore, the test compounds were safe.

2.2.2 Test Compounds are Effective in Reducing Lipid Content in Liver

Figure 1:
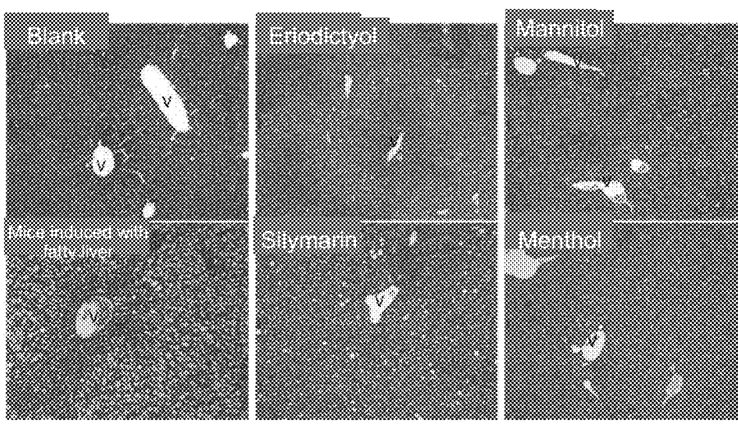
FIG. 1 shows liver tissue sections taken from mice that were induced fatty liver, and then treated with different test substances by groups for four weeks.

FIG. 1 shows that fatty liver was induced in mice whose liver cells near hepatic portal area (including the bile duct, portal vein, hepatic artery) were covered with many large vesicular fat droplets and hepatocellular ballooning appeared, indicating that the animal model of fatty liver was successfully established by induction.

The results of animal experiments shows that a plurality of test compounds exhibit the effects of lipid reduction in animal livers after administration for a period of 4 or 8 weeks. The results were shown in Tables 5-1 and 5-2.

TABLE 5-1

Test compounds can reduce liver lipids in animals.
(administration period of 4 weeks)

| Items Unit | TG in liver mg/g liver | TC in liver mg/g liver |
|---|---|---|
| Blank (n = 13) | 25.0 ± 9.2 *** | 2.5 ± 0.4 *** |
| HFD (n = 12) | 132.0 ± 69.2 | 6.6 ± 3.5 |
| Positive Control | | |
| silymarin 5.0 mg/kg (n = 6) | 46.8 ± 14.4 *** | 3.0 ± 0.9 *** |
| silymarin 1.5 mg/kg (n = 6) | 69.9 ± 32.3 ** | 3.7 ± 0.4 ** |
| Single test compound | | |
| phloridzin 2.5 mg/kg (n = 6) | 48.9 ± 14.1 *** | 2.9 ± 0.5 *** |
| eriodictyol 5.0 mg/kg (n = 6) | 54.2 ± 15.0 *** | 3.0 ± 0.9 *** |
| eriodictyol 2.5 mg/kg (n = 6) | 43.1 ± 13.1 *** | 3.8 ± 1.1 ** |
| sucralose 7.5 mg/kg (n = 6) | 56.8 ± 20.0 *** | 5.0 ± 0.9 |
| sucralose 1.5 mg/kg (n = 6) | 68.9 ± 37.5 ** | 3.0 ± 0.9 *** |
| menthol 1.5 mg/kg (n = 6) | 87.3 ± 72.3 * | 4.4 ± 3.5 * |
| mannitol 7.5 mg/kg (n = 6) | 53.8 ± 24.4 *** | 4.7 ± 1.2 |
| mannitol 4.5 mg/kg (n = 6) | 71.5 ± 45.5 *** | 7.2 ± 2.8 |
| mannitol 1.5 mg/kg (n = 6) | 61.8 ± 32.6 *** | 3.4 ± 0.6 *** |
| saccharin 1.5 mg/kg (n = 3) | 84.0 ± 41.4 | 2.8 ± 1.5 ** |
| puerarin 2.5 mg/kg (n = 6) | 89.4 ± 49.1 * | 6.7 ± 2.7 |
| hesperitin 2.5 mg/kg (n = 6) | 67.8 ± 16.6 *** | 3.7 ± 0.7 ** |
| Combinations of two test compounds | | |
| saccharin + mannitol 1.5 mg/kg + 1.5 mg/kg (n = 6) | 71.6 ± 32.0 *** | 8.5 ± 2.5 |
| menthol + mannitol 4.5 mg/kg + 4.5 mg/kg (n = 6) | 54.3 ± 11.8 *** | |
| menthol + mannitol 1.5 mg/kg + 1.5 mg/kg (n = 6) | 31.0 ± 11.2 *** | 6.9 ± 1.7 |

TABLE 5-1-continued

Test compounds can reduce liver lipids in animals.
(administration period of 4 weeks)

| Items<br>Unit | TG in liver<br>mg/g liver | TC in liver<br>mg/g liver |
|---|---|---|
| menthol + mannitol<br>.5 mg/kg + .5 mg/kg (n = 6) | 96.6 ± 77.4 | 5.9 ± 1.7 |
| Combinations of three test compounds | | |
| menthol + mannitol + eriodictyol<br>.5 mg/kg + .5 mg/kg + .8 mg/kg (n = 6) | 83.1 ± 50.9 * | 6.0 ± 2.3 |

Data were expressed as means ± SD.
Statistical difference resulted from ANOVA and LSD was denoted by words.
* $p < 0.05$,  $p < 0.01$, * $p < 0.005$, as compared with HFD.
TG: triglyceride
TC: total cholesterol
hesperitin
puerarin
eriodictyol
phloridzin
mannitol
menthol
sucralose
saccharin

TABLE 5-2

Test compounds can reduce liver lipids in animals
(administration period of 8 weeks)

| Items<br>Unit | TG in liver<br>mg/g liver | TC in liver<br>mg/g liver |
|---|---|---|
| Blank (n = 7) | 22.6 ± 3.8 *** | 3.8 ± 0.4 *** |
| HFD (n = 8) | 187.3 ± 91.2 | 12.1 ± 7.3 |
| Combinations of two test compounds | | |
| sucralose + mannitol<br>7.5 mg/kg + 7.5 mg/kg (n = 5) | 115.3 ± 36.2 * | 6.0 ± 3.0 ** |
| sucralose + mannitol<br>1.5 mg/kg + 1.5 mg/kg (n = 5) | 144.4 ± 59.9 | 6.0 ± 1.2 * |
| eriodictyol + mannitol<br>5.0 mg/kg + 7.5 mg/kg (n = 4) | 64.5 ± 35.7 *** | 3.6 ± 1.1 *** |
| eriodictyol + sucralose<br>5.0 mg/kg + 7.5 mg/kg (n = 6) | 41.1 ± 28.1 *** | 2.8 ± 1.0 *** |
| Combinations of three test compounds | | |
| sucralose + mannitol + eriodictyol<br>7.5 mg/kg + 7.5 mg/kg + 2.5 mg/kg (n = 6) | 39.7 ± 21.5 * | 4.6 ± 0.6 *** |

Data were expressed as means ± SD.
Statistical difference resulted from ANOVA and LSD was denoted by words.
* $p < 0.05$,  $p < 0.01$, * $p < 0.005$, as compared with HFD.
TG: triglyceride
TC: total cholesterol
eriodictyol
mannitol
sucralose The results show that TG and TC increase in the liver of mice where fatty liver was induced. Administration of test compounds, hesperitin, puerarin, eriodictyol, phloridzin, mannitol, menthol, and sucralose, respectively, reduces TG in liver significantly, where in particular 4-week treatment with eriodictyol accomplishes an excellent effect of about 67% reduction in liver TG content (p<0.005). In addition, administration of test compounds, hesperitin, eriodictyol, phloridzin, mannitol, menthol, sucralose, and saccharin, respectively, reduces TC in liver significantly, where in particular 4-week treatment with saccharin accomplishes an excellent effect of about 56% reduction in liver TC content (p<0.005).

With respect to administration of combinations of two test compounds, a combination of saccharin and mannitol, a combination of menthol and mannitol, a combination of sucralose and mannitol, a combination of eriodictyol and mannitol, or a combination of eriodictyol and sucralose can effectively reduce liver TG, where in particular, 4-week treatment with a combination of menthol and mannitol accomplishes an excellent effect of about 77% reduction in liver TG content (p<0.005); and 8-week treatment with a combination of eriodictyol and sucralose accomplishes an excellent effect of about 78% reduction in liver TG content (p<0.005). In addition, a combination of sucralose and mannitol, a combination of eriodictyol and mannitol, or a combination of eriodictyol and sucralose can significantly reduce liver TC content (p<0.005), where in particular, 8-week treatment with a combination of eriodictyol and sucralose accomplishes an excellent effect of about 77% reduction in liver TC content (p<0.005).

With respect to administration of combinations of three test compounds, a combination of menthol, mannitol, and eriodictyol or a combination of sucralose, mannitol, and eriodictyol can effectively reduce liver TG; where in particular, 8-week treatment with a combination of sucralose, mannitol, and eriodictyol accomplishes an excellent effect of about 79% reduction in liver TG content (p<0.005). In addition, a combination of sucralose, mannitol, and eriodictyol can significantly reduce liver TC.

2.2.3 Test Compounds are Effective in Reducing Liver Damages 2.2.3.1 Effects in Reducing Liver Fat and Liver Damages in Liver Tissues The results of animal experiments show that a plurality of test compounds exhibit the effects in reducing liver fat and liver damages in liver tissues during the test period of 4 weeks. FIG. 1 shows that the animals with fatty liver have damages in liver tissues, including many large vesicular fat droplets covering liver cells near hepatic portal area (including the bile duct, portal vein, hepatic artery) and hepatocellular ballooning. In contrast, after treatment with silymarin, menthol, eriodictyol or mannitol for 4 weeks, large vesicular fat droplets within liver cells in liver tissue section are significantly reduced, while a portion of small broken droplets is still observed in mice treated with silymarin but the morphology of the liver tissues of mice treated with menthol, eriodictyol, or mannitol is similar to that of animals in Blank group, indicating that the fatty liver diseases is milder. In addition, the NAS scoring results are shown in Table 6.

TABLE 6

The test compounds can reduce the condition of liver damage in animals.

| Items | NAS Unit mg/g liver |
|---|---|
| Blank (n = 13) | 0.7 ± 0.5*** |
| HFD (n = 12) | 3.3 ± 1.7 |
| Positive Control | |
| Silymarin 5.0 mg/kg (n = 6) | 0.8 ± 0.4*** |
| Silymarin 1.5 mg/kg (n = 6) | 1.5 ± 0.8* |
| Single test compound | |
| phloridzin 2.5 mg/kg (n = 6) | 1.8 ± 1.0 |
| eriodictyol 5.0 mg/kg (n = 6) | |
| eriodictyol 2.5 mg/kg (n = 6) | 1.5 ± 0.8* |
| sucralose 7.5 mg/kg (n = 6) | 1.8 ± 1.1 |
| sucralose 1.5 mg/kg (n = 6) | 1.8 ± 2.0 |
| menthol 1.5 mg/kg (n = 6) | 1.8 ± 1.6 |
| mannitol 7.5 mg/kg (n = 6) | 1.7 ± 0.8* |
| mannitol 4.5 mg/kg (n = 6) | 2.7 ± 1.9 |
| mannitol 1.5 mg/kg (n = 6) | 1.3 ± 0.8* |
| saccharin 1.5 mg/kg (n = 3) | |
| puerarin 2.5 mg/kg (n = 6) | |
| hesperitin 2.5 mg/kg (n = 6) | 1.7 ± 0.5 |
| Combinations of two test compounds | |
| saccharin + mannitol 1.5 mg/kg + 1.5 mg/kg (n = 6) | |
| menthol + mannitol 4.5 mg/kg + 4.5 mg/kg (n = 6) | 2.2 ± 1.5 |
| menthol + mannitol 1.5 mg/kg + 1.5 mg/kg (n = 6) | 0.7 ± 0.5*** |

TABLE 6-continued

The test compounds can reduce the condition of liver damage in animals.

| Items | NAS Unit mg/g liver |
|---|---|
| menthol + mannitol .5 mg/kg + .5 mg/kg (n = 6) | 2.5 ± 1.8 |
| Combinations of three test compounds | |
| menthol + mannitol + eriodictyol .5 mg/kg + .5 mg/kg + .8 mg/kg (n = 6) | 2.0 ± 1.4 |

Data were expressed as means ± SD.
Statistical difference resulted from ANOVA and LSD was denoted by words.
*p < 0.05,
**p < 0.01,
***p < 0.005, as compared with HFD.
hesperitin
puerarin
eriodictyol
phloridzin
mannitol
menthol
sucralose
saccharin NAS (Nonalcoholic Fatty Liver Disease Activity Score) indicates the activity score of non-alcoholic fatty liver diseases [Hepatology. 2005 June; 41(6):1313-21], involving comprehensive evaluation of the degree of steatosis, lobular inflammation, and hepatocyte ballooning. The score sheet is shown in Table 7. Higher score indicates severer liver damage.

TABLE 10

NAS Evaluation Project

| Items | Score | Degree | Definition and Description |
|---|---|---|---|
| steatosis | 0 | <5% | Refers to amount of surface area involved by steatosis as evaluated on low to medium power examination; minimal steatosis (<5%) receives a score of 0 to avoid giving excess weight to biopsies with very little fatty change. |
| | 1 | 5-33% | |
| | 2 | >33-66% | |
| | 3 | >66% | |
| lobular inflammation | 0 | No foci | Acidophil bodies are not included in this assessment, nor is portal inflammation. |
| | 1 | <2 foci/200x | |
| | 2 | 2-4 foci/200x | |
| | 3 | >4 foci/200x | |
| hepatocyte ballooning | 0 | None | |
| | 1 | few balloon cells | The term "few" means rare but definite ballooned hepatocytes as well as cases that are diagnostically borderline. |
| | 2 | Many cells/ prominent ballooning | Most cases with prominent ballooning also has mallory's hyaline, but Mallory's hyaline is not scored separately for the NAS. |

The results show that the mice with fatty liver have damages in liver tissues (NAS increasing). Administration of test compounds, eriodictyol and mannitol, respectively, can significantly reduce liver damages. It is notable that administration of a combination of two test compounds, menthol and mannitol, accomplishes an excellent effect, i.e. almost no liver damages appearing and the NAS being the same as that in the Blank.

2.2.3.2 Effect in Reducing Liver Dysfunction

The results of animal experiments show that a plurality of test compounds can reduce liver dysfunction in animals during administration period of 4 or 8 weeks. The results are showed in Table 8-1 and Table 8-2.

TABLE 8-1

Test compounds can reduce liver dysfunction in animals
(administration period of 4 weeks)

| Items<br>Unit | ALT<br>U/L | AST<br>U/L |
|---|---|---|
| blank (n = 13) | 32.6 ± 16.1 *** | 112.2 ± 53.9 *** |
| HFD (n = 12) | 70.1 ± 45.2 | 156.8 ± 100.8 |
| Positive Control | | |
| silymarin 5.0 mg/kg (n = 6) | 33.9 ± 9.3 *** | 168.1 ± 42.6 |
| silymarin 1.5 mg/kg (n = 6) | 43.8 ± 18.7 * | 153.6 ± 62.5 |
| Single test compound | | |
| mamiitol 7.5 mg/kg (n = 6) | 25.0 ± 10.8 *** | 63.3 ± 7.7 *** |
| mannitol 4.5 mg/kg (n = 6) | 44.5 ± 15.9 * | 107.6 ± 54.3 |
| mannitol 1.5 mg/kg (n = 6) | 40.8 ± 11.4 * | 187.2 ± 142.1 |
| sucralose 7.5 mg/kg (n = 6) | 32.3 ± 10.1 ** | 74.3 ± 18.6 ** |
| sucralose 1.5 mg/kg (n = 6) | 30.9 ± 16.8 *** | 127.0 ± 31.2 |
| eriodictyol 5.0 mg/kg (n = 5) | 41.4 ± 6.3 * | 161.4 ± 42.3 |
| eriodictyol 2.5 mg/kg (n = 6) | 33.7 ± 18.5 *** | 100.9 ± 42.0 |
| puerarin 2.5 mg/kg (n = 6) | 34.4 ± 14.7 *** | 66.9 ± 8.5 *** |
| phloridzin 2.5 mg/kg (n = 6) | 35.7 ± 9.1 *** | 161.9 ± 96.2 |
| hesperitin 2.5 mg/kg (n = 6) | 36.8 ± 22.1 ** | 72.4 ± 11.2 *** |
| menthol 1.5 mg/kg (n = 6) | 41.5 ± 13.7 * | 129.9 ± 37.1 |
| saccharin 1.5 mg/kg (n = 3) | 50.7 ± 29.7 | 170.4 ± 28.6 |
| Combinations of two test compounds | | |
| menthol + mannitol<br>.5 mg/kg + .5 mg/kg (n = 6) | 23.9 ± 17.8 *** | 60.4 ± 8.2 *** |
| menthol + mannitol<br>1.5 mg/kg + 1.5 mg/kg (n = 6) | 16.7 ± 4.3 *** | 59.8 ± 7.5 *** |
| sucralose + mannitol<br>7.5 mg/kg + 7.5 mg/kg (n = 6) | 45.5 ± 15.2 | 91.4 ± 21.8 * |
| sucralose + mannitol<br>1.5 mg/kg + 1.5 mg/kg (n = 6) | 52.4 ± 34.0 | 92.1 ± 23.0 * |
| eriodictyol + mannitol<br>5.0 mg/kg + 7.5 mg/kg (n = 4) | 43.4 ± 10.5 | 151.0 ± 54.2 |
| eriodictyol + sucralose<br>5.0 mg/kg + 7.5 mg/kg (n = 4) | 38.2 ± 10.9 * | 143.8 ± 67.6 |
| saccharin + mannitol<br>1.5 mg/kg + 1.5 mg/kg (n = 6) | 51.7 ± 54.2 | 70.0 ± 27.6 *** |
| Combinations of three test compounds | | |
| menthol + mannitol + eriodictyol<br>.5 mg/kg + .5 mg/kg + .8 mg/kg (n = 6) | 21.2 ± 8.7 *** | 54.8 ± 13.2 *** |

Data were expressed as means ± SD.
Statistical difference resulted from ANOVA and LSD was denoted by words.
* $p < 0.05$,  $p < 0.01$, * $p < 0.005$, as compared with HFD.
ALT: alanine aminotransferase
AST: aspartate transaminase
hesperitin
puerarin
hesperitin
puerarin
eriodictyol
phloridzin
mannitol
menthol
sucralose
saccharin

TABLE 8-2

Test compounds can reduce liver dysfunction in animals
(administration period of 8 weeks)

| Items<br>Unit | ALT<br>U/L | AST<br>U/L |
|---|---|---|
| Blank (n = 7) | 65.1 ± 21.5 *** | 22.6 ± 4.3 *** |
| HFD (n = 8) | 111.0 ± 26.2 | 109.4 ± 46.4 |
| Combinations of two test compounds | | |
| sucralose + mannitol<br>7.5 mg/kg + 7.5 mg/kg (n = 5) | 92.4 ± 16.5 | 49.5 ± 14.4 *** |
| sucralose + mannitol<br>1.5 mg/kg + 1.5 mg/kg (n = 4) | 112.5 ± 23.8 | 93.0 ± 26.0 |
| Combinations of three test compounds | | |
| sucralose + mannitol + eriodictyol<br>7.5 mg/kg + 7.5 mg/kg + 2.5 mg/kg (n = 6) | | 40.0 ± 12.2 *** |

Data were expressed as means ± SD.
Statistical difference resulted from ANOVA and LSD was denoted by words.
*p < 0.05, p < 0.01, * p < 0.005, as compared with HFD.
ALT: alanine aminotransferase
AST: aspartate transaminase
mannitol
sucralose ALT and AST are most commonly used as enzyme indicators to reflect the biochemical dysfunction of liver. Under normal circumstances, these enzymes present in liver cells. However, when liver cells are damaged, they will leak. Increases of serum ALT and AST values generally reflect liver inflammation and liver dysfunction.

The results show that animals with fatty liver have liver dysfunction (ALT and AST values increasing). Administration of test compounds, hesperitin, puerarin, eriodictyol, phloridzin, mannitol, menthol, sucralose, and saccharin, respectively, can significantly reduce ALT and AST values, where in particular, 4-week treatment with mannitol accomplishes an excellent effect of about 64% reduction in ALT value (p<0.005) and about 60% reduction in AST value (p<0.005).

With respect to administration of combinations of two test compounds, a combination of menthol and mannitol or a combination of eriodictyol and sucralose can significantly reduce ALT value; and a combination of menthol and mannitol, a combination of sucralose and mannitol, or a combination of saccharin and mannitol can significantly reduce AST value. In particular, 4-week treatment with a combination of menthol and mannitol accomplishes an excellent effect of about 76% reduction in ALT value (p<0.005) and about 62% reduction in AST value (p<0.005).

With respect to administration of combinations of three test compounds, a combination of sucralose, mannitol, and eriodictyol can significantly reduce ALT value (p<0.005).

2.2.4 the Test Compounds can Enhance Liver Antioxidant Activity

The results of animal experiments show that a plurality of test compounds are effective in enhancing liver antioxidant activity in animals during the test period of 4 weeks. The results are showed in Table 9-1 and Table 9-2.

TABLE 9-1

Test compounds can enhance liver antioxidant activity in animals
(Gpx and GSH)

| Items<br>Unit | Gpx<br>U/L | GSH<br>U/L |
|---|---|---|
| Blank (n = 10) | 2588.0 ± 524.5 | 1224.1 ± 95.5 |
| HFD (n = 8) | 2252.5 ± 395.2 | 1193.0 ± 203.8 |
| Positive Control | | |
| silymarin 5.0 mg/kg (n = 6) | 3358.3 ± 1205.3 *** | 1398.8 ± 396.5 |
| Single test compound | | |
| mannitol 7.5 mg/kg (n = 6) | 3738.3 ± 665.1 *** | 2147.7 ± 459.1 *** |
| mannitol 4.5 mg/kg (n = 6) | 3423.3 ± 547.8 *** | 1605.1 ± 305.9 ** |
| mannitol 1.5 mg/kg (n = 6) | 2580.0 ± 555.2 | 1502.5 ± 276.9 * |
| puerarin 2.5 mg/kg (n = 6) | 3581.7 ± 1056.7 *** | 1498.1 ± 150.0 * |
| sucralose 7.5 mg/kg (n = 6) | 3334.0 ± 377.7 ** | 1609.1 ± 201.1 ** |
| sucralose 1.5 mg/kg (n = 6) | 2995.0 ± 651.1 * | 1448.0 ± 281.5 |
| phloridzin 2.5 mg/kg (n = 6) | 3234.0 ± 505.1 ** | 1387.7 ± 168.2 |

TABLE 9-1-continued

Test compounds can enhance liver antioxidant activity in animals
(Gpx and GSH)

| Items Unit | Gpx U/L | GSH U/L |
|---|---|---|
| hesperitin 2.5 mg/kg (n = 6) | 3133.3 ± 376.9 * | 1742.6 ± 241.5 *** |
| eriodictyol 2.5 mg/kg (n = 6) | 3083.3 ± 378.9 ** | 1302.0 ± 241.1 |
| menthol 1.5 mg/kg (n = 6) | 2921.7 ± 640.2 | 1432.7 ± 104.0 |

Data were expressed as means ± SD.
Statistical difference resulted from ANOVA and LSD was denoted by words.
* p < 0.05,  p < 0.01, * p < 0.005, as compared with HFD.
Gpx: glutathione peroxidase
GSH: glutathione
hesperitin
puerarin
hesperitin
puerarin
eriodictyol
phloridzin
mannitol
menthol
sucralose

TABLE 9-2

Test compounds can enhance liver antioxidant activity in animals
(Grd and SOD)

| Items Unit | Grd U/L | SOD U/L |
|---|---|---|
| Blank (n = 10) | 123.5 ± 30.9 | 380.3 ± 38.8 |
| HFD (n = 8) | 82.1 ± 21.7 | 371.7 ± 49.3 |
| Positive Control | | |
| silymarin 5.0 mg/kg (n = 6) single test compound | 88.9 ± 29.2 | 435.9 ± 59.2 * |
| mannitol 7.5 mg/kg (n = 6) | 117.6 ± 32.0 ** | 462.8 ± 52.8 |
| mannitol 4.5 mg/kg (n = 6) | 110.1 ± 18.4 * | 429.2 ± 85.2 |
| mannitol 1.5 mg/kg (n = 6) | 95.3 ± 22.1 | 367.3 ± 35.6 |
| puerarin 2.5 mg/kg (n = 6) | 99.0 ± 17.2 | 434.5 ± 59.8 |
| sucralose 7.5 mg/kg (n = 6) | 90.4 ± 17.2 | 399.0 ± 34.5 |
| sucralose 1.5 mg/kg (n = 6) | 100.0 ± 18.6 | 373.0 ± 50.4 |
| phloridzin 2.5 mg/kg (n = 6) | 82.2 ± 33.6 | 411.5 ± 87.5 |
| hesperitin 2.5 mg/kg (n = 6) | 102.5 ± 28.3 | 408.3 ± 66.7 |
| eriodictyol 2.5 mg/kg (n = 6) | 86.9 ± 15.7 | 385.9 ± 34.0 |
| menthol 1.5 mg/kg (n = 6) | 95.2 ± 16.2 | 427.9 ± 41.9 |

Data were expressed as means ± SD.
Statistical difference resulted from ANOVA and LSD was denoted by words.
* p < 0.05,  p < 0.01, *p < 0.005, as compared with HFD.
Grd: Glutathione reductase
SOD: Superoxide dismutase
hesperitin
puerarin
hesperitin
puerarin
eriodictyol
phloridzin
mannitol
menthol
sucralose Gpx, GSH, Grd and SOD are common members of liver antioxidant systems that can reduce oxidative stress in the liver and prevent liver from damages caused by oxidative stress. Increases of Gpx, GSH, Grd and SOD values indicate liver maintaining better antioxidant activity.

The results show that the mice with fatty liver have reduced antioxidant activity. Administration of test compounds, hesperitin, puerarin, eriodictyol, phloridzin and mannitol, respectively, can significantly enhance antioxidant activity, where in particular 4-week treatment with mannitol accomplishes an excellent effect of substantial increases in Gpx, GSH, Grd, and SOD levels (p<0.005).

Given the above, the compounds provided in the present invention can reduce fat content in the liver, reduce liver damages, and enhance liver antioxidant activity. These compounds belong to low-molecular natural plant phenolic compounds, and exist extensively in fruits and vegetables, grains, roots, flowers, tea and red wine, etc. In addition, these compounds have been confirmed safe through animal experiments and found having potential to be developed into health food or drugs for reducing liver fat and ameliorating associated disorders, such as fatty liver diseases, acute and chronic alcoholic fatty liver diseases, acute and chronic non-alcoholic fatty liver diseases (NAFLD), acute and chronic alcoholic hepatitis, acute and chronic non-alcoholic steatohepatitis, non-alcoholic cirrhosis, and alcoholic cirrhosis (ICD-9-CM diagnosis Codes: 571.8, 571.0, 571.1, 571.2, 571.3, 571.4, 571.5, 571.9).

REFERENCES

1. Brunt E M, Janney C G, Di Bisceglie A M, Neuschwander-Tetri B A and Bacon B R. (1999) Nonalcoholic steatohepatitis: a proposal for grading and staging the histological lesions. *Am J Gastroenterol* 94: 2467-2674.
2. Clark J M and Diehl A M. (2003) Nonalcoholic fatty liver disease: an underrecognized cause of cryptogenic cirrhosis. *JAMA* 289: 300-304.
3. Carlisle R, Galambos J T, Warren W D. (1979) The relationship between conventional liver tests, quantitative function tests, and histopathology in cirrhosis. *Dig Dis Sci* 24: 358-362.
3. Cua I H. & George J. (2005) Non-alcoholic fatty liver disease. *Hosp Med* 66: 106-111.
4. Day C P and James O F W. (1998) Steatohepatitis: a tale of two 'hits'?*Gastroenterology* 114: 842-845.
5. Dowman J K, Tomlinson J W and Newsome P N. (2010) Pathogenesis of non-alcoholic fatty liver disease. *QJ Med* 103: 71-83.
6. Food and Drug Administration (2003) Guidance for Industry: Pharmacokinetics in Patients with Impaired Hepatic Function: Study Design, Data Analysis, and Impact on Dosing and Labeling. US Department of Health and Human Services, FDA, Center for Drug Evaluation and Research, Center for Biologics Evaluation and Research.

7. French S W. (2001) Intragastric ethanol infusion model for cellular and molecular studies alcoholic liver disease. *J Biomed Sci* 8: 20-27.
8. Gauthier M S, Favier R and Lavoie J M. (2006) Time course of the development of non-alcoholic hepatic steatosis in response to high-fat diet-induced obesity in rats. *Br J Nutr* 95: 273-281.
9. Guo H X, Liu D H, Ma Y, Liu J F, Wang Y, Du Z Y, Wang X, Shen J K and Peng H L. (2009) Long-term baicalin administration ameliorates metabolic disorders and hepatic steatosis in rats given a high-fat diet. *Acta Pharmacol Sin* 30: 1505-1512.
10. Herold C, Heinz R, Niedobitek G, Schneider T, Hahn E G, Schuppan D. (2001) Quantitative testing of liver function in relation to fibrosis in patients with chronic hepatitis B and C. *Liver* 21: 260-265.
11. Hu O Y, Tang H S, Chang C L. (1994) The influence of chronic lobular hepatitis on pharmacokinetics of cefoperazone—a novel galactose single-point method as a measure of residual liver function. *Biopharm Drug Dispos* 15: 563-576.
12. Hu O Y, Hu T M and Tang H S. (1995) Determination of galactose in human blood by high-performance liquid chromatography: comparison with an enzymatic method and application to the pharmacokinetic study of galactose in patients with liver dysfunction. *J Pharm Sci* 84: 231-235.
13. Hu O Y, Tang H S, Sheeng T Y, Chen T C and Curry S H. (1995) Pharmacokinetics of promazine in patients with hepatic cirrhosis—correlation with a novel galactose single point method. *J Pharm Sci* 84: 111-114.
14. Keiding S, Johansen S, Tonnesen K. (1977) Kinetics of ethanol inhibition of galactose elimination in perfused pig liver. *Scand J Clin Lab Invest* 37: 487-494.
15. Keiding S, Johansen S, Winkler K. (1982) Hepatic galactose elimination kinetics in the intact pig. *Scand J Clin Lab Invest* 42: 253-259.
16. Knodell R G, Ishak K G, Black W C, Chen T S, Craig R, Kaplowitz N, Kiernan T W and Wollman J. (1981) Formulation and application of a numerical scoring system for assessing histological activity in asymptomatic chronic active hepatitis. *Hepatology* 1: 431-435.
17. Leclercq I A, Farrell G C and Field J. (2000) CYP2E1 and CYP4A as microsomal catalysts of lipid peroxides in murine nonalcoholic steatohepatitis. *J Clin Invest* 105: 1067-1075.
18. Lindskov J. (1982) The quantitative liver function as measured by the galactose elimination capacity. I. Diagnostic value and relations to clinical, biochemical, and histological findings in patients with steatosis and patients with cirrhosis. *Acta Med Scand* 212: 295-302.
19. Lin S C, Lin Y H, Chen C F, Chung C Y and Hsu S H. (1997) The hepatoprotective and therapeutic effects of propolis ethanol extract on chronic alcohol-induced liver injuries. *Am J Chin Med* 25: 325-332.
20. Liu C H, Huang M T and Huang P C. (1995) Sources of triacylglycerol accumulation in livers of rats fed a cholesterol-supplemented diet. *Lipids* 30: 527-531.
21. Mulhall B P, One J P and Younossi Z M. (2002) Non-alcoholic fatty liver disease: an overview. *J Gastroenterol Hepatol* 17: 1130-1143.
22. Nanji A A. (2004) Another animal model for nonalcoholic steatohepatitis: how close to the human condition? *Am J Clin Nutr* 79: 350-351.
23. Nistor A, Bulla A, Filip D A and Radu A. (1987) The hyperlipidemic hamster as a model of experimental atherosclerosis. *Atherosclerosis* 68: 159-173.
24. Sanyal A J, Campbell-Sargent C and Mirshahi F. (2001) Nonalcoholic steatohepatitis: association of insulin resistance and mitochondrial abnormalities. *Gastroenterology* 120: 1183-1192.
25. Sass D A, Chang P and Chopra, K B. (2005) Nonalcoholic fatty liver disease: a clinical review. *Dig Dis Sci* 50: 171-180.
26. Schaefer E J. (1997) Effects of dietary fatty acids on lipoproteins and cardiovascular disease risk: summary. *Am J Clin Nutr* 65: 1655S-1656S.
27. Schaffner F and Thaler H. (1986) Nonalcoholic fatty liver disease. *Prog Liver Dis* 8: 283-298.
28. Sullivan M P, Cerda J J, Robbins F L, Burgin C W and Beatty R J. (1993) The gerbil, hamster, and guinea pig as rodent models for hyperlipidemia. *Lab Anim Sci* 43: 575-578.
29. Tang H S and Hu O Y. (1992) Assessment of liver function using a novel galactose single point method. *Digestion* 52: 222-231.
30. Tominaga K, Kurata J H and Chen Y K. (1995) Prevalence of fatty liver in Japanese children and relationship to obesity. *Dig Dis Sci* 40: 2002-2009.
31. Zhang Z, Wang H, Jiao R, Peng C, Wong Y M, Yeung V S, Huang Y and Chen Z Y. (2009) Choosing hamsters but not rats as a model for studying plasma cholesterol lowering activity of functional foods. *Mol Nutr Food Res* 53: 921-930.
32. Zou Y, Li J, Lu C, Wang J, Ge J, Huang Y, Zhang L and Wang Y. (2006) High-fat emulsion-induced rat model of nonalcoholic steatohepatitis. *Life Sci* 79: 1100-1107.
33. Zhang D, Xie L, Jia G, Cai S, Ji B, Liu Y, Wu W, Zhou F, Wang A, Chu L, Wei Y, Liu J and Gao F. (2011) Comparative study on antioxidant capacity of flavonoids and their inhibitory effects on oleic acid-induced hepatic steatosis in vitro. *Eur J Med Chem* 46: 4548-4558.

What is claimed is:

1. A method for ameliorating liver diseases caused by fatty liver or other associated disorders in a subject in need thereof comprising administering to the subject a composition comprising
    a compound as an active agent for ameliorating the liver diseases caused by fatty liver or other associated disorders, wherein the compound is selected from the group consisting of sodium lauryl sulfate, menthol, sucralose, mannitol, sorbitol, saccharin, sodium benzoate, oxide red, butylated hydroxyanisole and any combinations thereof, or
    a combination as an active agent for ameliorating the liver diseases caused by fatty liver or other associated disorders, wherein the combination is selected from the group consisting of (1) a combination of saccharin and mannitol, (2) a combination of menthol and mannitol, (3) a combination of sucralose and mannitol, (4) a combination of eriodictyol and mannitol, (5) a combination of eriodictyol and sucralose, (6) a combination of menthol, mannitol, and eriodictyol, and (7) a combination of sucralose, mannitol, and eriodictyol.

2. The method of claim 1, wherein the method comprises administering the compound as the active agent, wherein the compound is selected from the group consisting of sodium lauryl sulfate, menthol, sucralose, mannitol, sorbitol, saccharin, sodium benzoate, oxide red, butylated hydroxyanisole and any combinations thereof.

3. The method of claim 1, wherein the compound is selected from the group consisting of mannitol, menthol, sucralose, saccharin, and any combinations thereof.

4. The method of claim 1, wherein the composition further comprises another compound as the active agent which is selected from the group consisting of puerarin, phloridzin, sinensetin, (−)-epigallocatechin, kaempferol, ursolic acid, silymarin, (+)-limonene, hesperidin, (−)-epicatechin-3-gallate, silybin, formononetin, myristic acid ethyl ester, eicosapentaenoic acid (EPA), wongonin, povidone K-30, protocatechuic acid, umbelliferone, hesperitin, nordihydroguaiaretic acid, neohesperidin, naringin, (−)-epicatechin, glycyrrhizin, baicalin, quercitrin, baicalein, (±)-catechin, and any combination thereof.

5. The method of claim 1, wherein an amount of the compound or the combination that is administered is an amount effective in reducing a liver fat content of the subject.

6. The method of claim 1, wherein an amount of the compound or the combination that is administered is an amount effective in reducing a fat content in liver cells of the subject.

7. The method of claim 1, wherein an amount of the compound or the combination that is administered is an amount effective in reducing liver damages of the subject.

8. The method of claim 7, wherein the liver damages include liver tissue damages or liver dysfunction.

9. The method of claim 1, wherein an amount of the compound or the combination that is administered is an amount effective in enhancing liver antioxidant activities.

10. The method of claim 1, wherein the liver disease or other associated disorders are selected from the group consisting of acute and chronic alcoholic fatty liver, acute and chronic non-alcoholic fatty liver, acute and chronic alcoholic hepatitis, acute and chronic non-alcoholic steatohepatitis, non-alcoholic cirrhosis and alcoholic cirrhosis.

11. The method of claim 1, wherein the subject is a patient with nonalcoholic fatty liver diseases or obese individuals.

12. The method of claim 1, wherein the composition is formulated as a drug, a food additive, or health food.

13. The method of claim 1, wherein the composition further comprises a pharmaceutically acceptable carrier, and said pharmaceutically acceptable carrier is not any of the compound or the combination.

14. The method of claim 8, wherein the liver damages exhibit one or more characteristics selected from the group consisting of steatosis, lobular inflammation, hepatocyte ballooning, and vesicular fat droplets produced by liver cells.

15. The method of claim 8, wherein the liver damages are biochemical dysfunction of liver to be determined from the activity of alanine aminotransferase (ALT) or aspartate transaminase (AST).

* * * * *